US009681879B2

(12) United States Patent
del Rio et al.

(10) Patent No.: US 9,681,879 B2
(45) Date of Patent: Jun. 20, 2017

(54) SURGICAL DRILL INSTRUMENT WITH MOTOR AND LOCKING MECHANISM TO RECEIVE AN ATTACHMENT AND A CUTTING BURR

(71) Applicant: DePuy Synthes Products, Inc., Raynham, MA (US)

(72) Inventors: Eddy H. del Rio, Royal Palm Beach, FL (US); Duane Jeffrey Enck, West Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/171,232

(22) Filed: Jun. 2, 2016

(65) Prior Publication Data

US 2016/0270799 A1   Sep. 22, 2016

Related U.S. Application Data

(63) Continuation of application No. 14/833,401, filed on Aug. 24, 2015, now Pat. No. 9,381,023, which is a
(Continued)

(51) Int. Cl.
*A61B 17/16* (2006.01)
*A61B 17/32* (2006.01)
*A61B 17/00* (2006.01)

(52) U.S. Cl.
CPC ........ *A61B 17/1615* (2013.01); *A61B 17/162* (2013.01); *A61B 17/1617* (2013.01);
(Continued)

(58) Field of Classification Search
CPC ................ A61B 17/16; A61B 17/1613; A61B 17/1615; A61B 17/1617; A61B 17/162;
(Continued)

(56) References Cited

U.S. PATENT DOCUMENTS

| 170,604 A | 11/1875 | Williams |
| 170,694 A | 12/1875 | Williams |

(Continued)

FOREIGN PATENT DOCUMENTS

| CN | 2631675 | 3/2003 |
| CN | 1406700 | 4/2003 |

(Continued)

OTHER PUBLICATIONS

Office Action, dated Dec. 16, 2014, received in connection with JP Application No. 2014503639. (English Translation).
(Continued)

*Primary Examiner* — Christian Sevilla
*Assistant Examiner* — Eric S Gibson
(74) *Attorney, Agent, or Firm* — Meunier Carlin & Curfman LLC

(57) ABSTRACT

A surgical apparatus having a locking mechanism that receives a cutting burr and that may include a loading and running position. The locking mechanism may include a motor driven spindle that carries a locking pawl and a detent pawl that lock the cutting burr in place an prevent the cutting burr from inadvertently falling out of the surgical drill instrument when in its load position. A diamond-shaped portion of the cutting burr may be formed in a six-sided diamond configuration and a perpendicular back end surface. The end of the cutting burr may include another diamond-shaped portion formed in a six-sided diamond shape surface that mates with a complementary surface formed in the receiving end of the spindle of the motor/locking mechanism. In an aspect, the attachment of the cutting burr is such that the cutting burr has substantially zero axial movement and runs true in the running condition.

20 Claims, 6 Drawing Sheets

Related U.S. Application Data continuation of application No. 14/456,383, filed on Aug. 11, 2014, now Pat. No. 9,113,917, which is a continuation of application No. 13/082,029, filed on Apr. 7, 2011, now Pat. No. 8,801,713.

(52) U.S. Cl.
CPC .............. *A61B 17/32002* (2013.01); *A61B 2017/00477* (2013.01); *Y10T 29/49826* (2015.01); *Y10T 29/49828* (2015.01); *Y10T 279/17777* (2015.01)

(58) Field of Classification Search
CPC ............ A61B 17/1622; A61B 17/1624; A61B 17/1628; A61B 17/1631; Y10T 279/17761; Y10T 279/17769; Y10T 279/17777
USPC ....... 606/79–81, 84, 85, 167, 169–171, 180; 81/177.85, 438; 279/35, 37, 77, 78, 89, 279/106, 107, 131, 156; 403/383; 408/226

See application file for complete search history.

(56) References Cited

U.S. PATENT DOCUMENTS

| | | | | |
|---|---|---|---|---|
| RE8,360 E | | 8/1878 | Williams | |
| 233,707 A | * | 10/1880 | Starr | B23B 31/103 279/77 |
| 233,709 A | * | 10/1880 | Starr | A61C 1/141 279/80 |
| 269,627 A | * | 12/1882 | Bonner | B23G 1/22 279/35 |
| 283,745 A | * | 8/1883 | Bartlett | B23G 1/04 279/76 |
| 287,683 A | | 10/1883 | Johnston et al. | |
| 302,870 A | * | 7/1884 | Starr | A61C 1/141 279/77 |
| 327,558 A | * | 10/1885 | Kuder | B44B 3/065 269/165 |
| 359,798 A | * | 3/1887 | Mann | B23B 31/18 279/35 |
| 415,983 A | * | 11/1889 | Starr | A61C 3/02 433/165 |
| 418,108 A | * | 12/1889 | Browne | A61C 3/02 433/165 |
| 474,011 A | * | 5/1892 | Harrison | A61C 3/02 433/165 |
| 553,226 A | * | 1/1896 | Brockett | B23B 31/18 279/35 |
| 748,398 A | * | 12/1903 | Middleton | B23B 51/123 279/103 |
| 988,154 A | * | 3/1911 | Thiemer | B23D 43/02 279/19.4 |
| 988,903 A | * | 4/1911 | Smith | B23B 31/005 175/320 |
| 1,135,057 A | * | 4/1915 | Schultis | B23G 5/12 279/106 |
| 1,188,533 A | * | 6/1916 | Cobey | B23B 31/1246 279/156 |
| 1,433,590 A | * | 10/1922 | Ziegler | B23G 1/46 279/158 |
| 1,503,962 A | * | 8/1924 | Milliken | B24B 19/03 279/106 |
| 1,578,397 A | * | 3/1926 | Cone | B23B 13/125 279/35 |
| 1,717,663 A | | 6/1929 | Checkley | |
| 1,726,012 A | * | 8/1929 | Bilz | B25C 1/02 227/147 |
| 1,862,337 A | * | 6/1932 | Emrick | B23B 31/028 279/74 |
| 1,947,957 A | * | 2/1934 | Tiliman | B23B 31/185 269/234 |
| 2,012,280 A | * | 8/1935 | Johansen | E21B 3/04 175/414 |
| 2,101,347 A | * | 12/1937 | Robinette | B23G 5/064 408/222 |
| 2,367,863 A | * | 1/1945 | Grey | B23B 31/14 279/131 |
| 2,390,950 A | * | 12/1945 | Lanfranconi | B23B 31/005 408/226 |
| 2,405,018 A | * | 7/1946 | Crowley | B21D 51/36 269/23 |
| 2,448,817 A | * | 9/1948 | McArthur | F16B 9/02 248/501 |
| 2,473,380 A | * | 6/1949 | Ljunggren | B23B 31/32 279/139 |
| 2,494,166 A | * | 1/1950 | Drissner | B23B 31/18 279/106 |
| 2,543,290 A | * | 2/1951 | Johansson | B23B 31/103 279/78 |
| 2,614,781 A | * | 10/1952 | Engel | A47B 91/08 248/149 |
| 2,686,682 A | * | 8/1954 | Csaki | B23B 31/14 279/131 |
| 2,740,974 A | * | 4/1956 | Lewis | B23G 5/064 408/222 |
| 2,769,643 A | * | 11/1956 | Denzler | B23B 31/201 279/37 |
| 2,787,010 A | * | 4/1957 | Uphoff | B23G 5/06 408/204 |
| 2,874,985 A | * | 2/1959 | March | B23Q 3/12 279/8 |
| 2,939,643 A | * | 6/1960 | Barsam, Jr. | G03B 21/43 242/545 |
| 2,955,831 A | * | 10/1960 | Zandberg | A61C 1/142 279/78 |
| 3,046,029 A | * | 7/1962 | Weber | C30B 15/32 279/37 |
| 3,054,308 A | * | 9/1962 | Larry | B23B 51/0486 408/226 |
| 3,084,898 A | * | 4/1963 | Miller | E21B 33/06 137/601.02 |
| 3,136,347 A | * | 6/1964 | Linquist | B23B 31/005 279/89 |
| RE25,804 E | * | 6/1965 | Misuraca | B43L 19/0006 279/106 |
| 3,252,667 A | * | 5/1966 | Miller | B65H 75/242 242/571.6 |
| 3,466,971 A | * | 9/1969 | Meyer | B23Q 3/15553 279/37 |
| 3,533,638 A | * | 10/1970 | Sedgwick | B23B 31/103 279/37 |
| 3,574,374 A | * | 4/1971 | Keller | A61B 17/1633 403/328 |
| 3,589,826 A | * | 6/1971 | Fenn | B23B 31/005 408/226 |
| 3,596,917 A | * | 8/1971 | Meyer | B23B 31/18 279/103 |
| 3,599,996 A | * | 8/1971 | Holt | B23B 31/18 279/37 |
| 4,032,163 A | * | 6/1977 | Holt | B23B 31/18 279/118 |
| 4,055,185 A | * | 10/1977 | Waldron | A61B 17/1633 279/77 |
| 4,073,497 A | * | 2/1978 | Flagg | B23B 31/40 242/599.2 |
| 4,114,276 A | * | 9/1978 | Malata | A61C 1/14 279/145 |
| 4,115,024 A | | 9/1978 | Süssmuth | |
| 4,131,165 A | * | 12/1978 | Wanner | B23Q 3/12 173/133 |
| 4,298,074 A | * | 11/1981 | Mattchen | A61B 17/1624 173/129 |
| 4,303,252 A | * | 12/1981 | Snider | B23B 31/18 279/106 |

(56) References Cited

U.S. PATENT DOCUMENTS

| | | | | |
|---|---|---|---|---|
| 4,325,661 A * | 4/1982 | Tickins | B23Q 13/00 | 279/156 |
| 4,374,481 A * | 2/1983 | Brodie | B25B 13/44 | 279/107 |
| 4,565,472 A * | 1/1986 | Brennsteiner | B23B 31/005 | 175/414 |
| 4,632,195 A * | 12/1986 | Emmerich | E21B 17/046 | 175/320 |
| 4,710,075 A * | 12/1987 | Davison | A61B 17/16 | 33/512 |
| 4,984,667 A * | 1/1991 | Tjaden | F16D 7/025 | 137/384.2 |
| 5,037,251 A * | 8/1991 | Roth | B23B 31/005 | 408/222 |
| 5,074,025 A * | 12/1991 | Willard, III | B23B 31/005 | 279/103 |
| 5,152,642 A | 10/1992 | Pitts et al. | | |
| 5,218,890 A * | 6/1993 | Christ, Jr. | B23B 31/18 | 279/35 |
| 5,271,697 A * | 12/1993 | Johnson | B23B 31/1071 | 279/75 |
| 5,421,682 A * | 6/1995 | Obermeier | B25D 17/088 | 279/19.3 |
| 5,433,562 A * | 7/1995 | Phillips | B23B 31/261 | 279/125 |
| 5,466,101 A * | 11/1995 | Meyen | B25D 17/088 | 279/19.4 |
| 5,542,846 A * | 8/1996 | Quinn | A61C 1/141 | 279/106 |
| 5,601,560 A * | 2/1997 | Del Rio | A61B 17/162 | 408/231 |
| 5,630,818 A * | 5/1997 | Del Rio | A61B 17/162 | 279/77 |
| 5,658,305 A | 8/1997 | Baker | | |
| 5,664,792 A * | 9/1997 | Tseng | B23B 31/103 | 16/422 |
| 5,735,535 A * | 4/1998 | McCombs | A61B 17/162 | 279/131 |
| 5,741,263 A * | 4/1998 | Umber | A61B 17/162 | 279/75 |
| 5,820,136 A * | 10/1998 | Han | B23B 31/14 | 279/131 |
| 5,833,246 A * | 11/1998 | Trott | B23B 31/14 | 279/131 |
| 5,833,704 A * | 11/1998 | McCombs | A61B 17/162 | 408/226 |
| 5,888,200 A * | 3/1999 | Walen | A61B 17/1622 | 606/167 |
| 5,904,687 A * | 5/1999 | Del Rio | A61B 17/162 | 408/231 |
| 5,921,563 A * | 7/1999 | Huggins | B23B 31/14 | 279/131 |
| 5,941,891 A * | 8/1999 | Walen | A61B 17/1622 | 606/167 |
| 5,957,634 A * | 9/1999 | Carpinetti | B23B 31/1071 | 279/143 |
| 6,033,408 A * | 3/2000 | Gage | A61B 17/162 | 173/218 |
| 6,045,564 A * | 4/2000 | Walen | A61B 17/1622 | 606/1 |
| 6,129,363 A * | 10/2000 | Mack | B23B 31/1215 | 279/158 |
| 6,135,461 A | 10/2000 | Below et al. | | |
| RE37,358 E * | 9/2001 | Del Rio | A61B 17/162 | 408/231 |
| 6,302,408 B1 | 10/2001 | Zierpka | | |
| 6,341,926 B1 * | 1/2002 | Liu | B23B 31/005 | 408/222 |
| 6,409,181 B1 | 6/2002 | Hsueh | | |
| 6,533,235 B1 * | 3/2003 | Dymerski | B60N 2/0232 | 248/421 |
| 6,533,291 B2 * | 3/2003 | Huggins | B23B 31/1238 | 279/137 |
| 6,572,311 B2 * | 6/2003 | Vasudeva | B23B 31/005 | 408/226 |
| 6,607,533 B2 * | 8/2003 | Del Rio | A61B 17/162 | 408/226 |
| 6,623,220 B2 | 9/2003 | Nuss et al. | | |
| 6,705,807 B1 * | 3/2004 | Rudolph | B23B 51/0426 | 279/143 |
| 6,725,749 B1 * | 4/2004 | Liou | B25B 23/0035 | 81/438 |
| 6,733,218 B2 * | 5/2004 | Del Rio | A61B 17/162 | 279/79 |
| 6,769,846 B2 * | 8/2004 | Campbell, Jr. | F16D 43/16 | 279/131 |
| 6,780,189 B2 * | 8/2004 | Tidwell | A61B 17/1633 | 606/170 |
| 7,011,661 B2 * | 3/2006 | Riedel | A61B 17/162 | 606/170 |
| 7,028,589 B1 * | 4/2006 | Cheng | B25B 23/0035 | 81/125 |
| 7,066,940 B2 * | 6/2006 | Riedel | A61B 17/162 | 606/167 |
| 7,114,728 B2 * | 10/2006 | Chen | B23B 31/107 | 279/155 |
| 7,140,817 B1 * | 11/2006 | Phillips | B23B 31/008 | 144/136.95 |
| 7,207,400 B2 * | 4/2007 | Bise | E21B 17/03 | 175/320 |
| 7,258,349 B2 * | 8/2007 | Frauhammer | B23Q 3/12 | 279/19 |
| 7,316,529 B2 * | 1/2008 | Phillips | B23B 31/008 | 144/136.95 |
| 7,367,762 B2 * | 5/2008 | Takase | B23B 31/263 | 408/239 R |
| 7,465,309 B2 * | 12/2008 | Walen | A61B 17/1615 | 606/167 |
| 7,712,746 B2 * | 5/2010 | Manschitz | B23B 31/107 | 279/143 |
| 7,845,428 B2 * | 12/2010 | Sakamaki | B23B 31/1071 | 173/104 |
| 8,273,097 B2 * | 9/2012 | Malla | A61B 17/32002 | 606/167 |
| 8,403,338 B2 * | 3/2013 | Hangleiter | B23B 31/265 | 279/35 |
| 8,690,876 B2 * | 4/2014 | del Rio | A61B 17/162 | 408/226 |
| 8,801,713 B2 * | 8/2014 | del Rio | A61B 17/1615 | 279/78 |
| 9,113,917 B2 * | 8/2015 | del Rio | A61B 17/1615 | |
| 9,381,023 B2 * | 7/2016 | del Rio | A61B 17/1615 | |
| 9,402,638 B2 | 8/2016 | del Rio et al. | | |
| 2001/0006280 A1 * | 7/2001 | Hangleiter | B23B 31/261 | 279/37 |
| 2001/0042964 A1 * | 11/2001 | Bedi | B25B 15/001 | 279/30 |
| 2002/0009341 A1 | 1/2002 | Vasudeva | | |
| 2002/0058958 A1 * | 5/2002 | Walen | A61B 17/1615 | 606/170 |
| 2002/0151902 A1 * | 10/2002 | Riedel | A61B 17/162 | 606/80 |
| 2002/0159850 A1 | 10/2002 | Ravid | | |
| 2002/0165549 A1 * | 11/2002 | Owusu-Akyaw | A61B 17/1628 | 606/80 |
| 2003/0060829 A1 | 3/2003 | del Rio et al. | | |
| 2003/0060841 A1 * | 3/2003 | Del Rio | A61B 17/162 | 606/167 |
| 2003/0130663 A1 * | 7/2003 | Walen | A61B 17/1615 | 606/80 |
| 2003/0163134 A1 * | 8/2003 | Riedel | A61B 17/162 | 606/79 |
| 2005/0096661 A1 * | 5/2005 | Farrow | A61B 17/1628 | 606/79 |
| 2006/0049587 A1 | 3/2006 | Cornwell | | |
| 2006/0053974 A1 | 3/2006 | Blust et al. | | |

(56) References Cited

U.S. PATENT DOCUMENTS

| | | | | |
|---|---|---|---|---|
| 2008/0119863 A1* | 5/2008 | Mellier | A61B 17/0469 | |
| | | | 606/99 | |
| 2008/0208195 A1* | 8/2008 | Shores | A61B 17/162 | |
| | | | 606/79 | |
| 2008/0208229 A1* | 8/2008 | Tidwell | A61B 17/1628 | |
| | | | 606/167 | |
| 2009/0146421 A1 | 6/2009 | Engdahl | | |
| 2009/0273146 A1* | 11/2009 | Dezheng | B23D 51/10 | |
| | | | 279/78 | |
| 2009/0326540 A1* | 12/2009 | Estes | A61B 17/14 | |
| | | | 606/82 | |
| 2010/0063524 A1* | 3/2010 | McCombs | A61B 17/162 | |
| | | | 606/167 | |
| 2010/0219594 A1* | 9/2010 | Nash | B25B 23/0035 | |
| | | | 279/77 | |
| 2012/0003057 A1* | 1/2012 | Leyba | B23B 31/005 | |
| | | | 408/226 | |
| 2012/0259336 A1* | 10/2012 | del Rio | A61B 17/162 | |
| | | | 606/80 | |
| 2012/0259337 A1* | 10/2012 | del Rio | A61B 17/1615 | |
| | | | 606/80 | |
| 2012/0275875 A1* | 11/2012 | Gischus | B23B 31/005 | |
| | | | 408/226 | |
| 2013/0130663 A1 | 5/2013 | Jung et al. | | |
| 2014/0303624 A1 | 10/2014 | del Rio et al. | | |
| 2015/0032111 A1* | 1/2015 | del Rio | A61B 17/1615 | |
| | | | 606/80 | |

FOREIGN PATENT DOCUMENTS

| | | | | |
|---|---|---|---|---|
| CN | 1672641 | 9/2005 | | |
| CN | 2774405 | 4/2006 | | |
| CN | 2882550 | 3/2007 | | |
| CN | 101365390 | 2/2009 | | |
| JP | 02009507 A | * | 1/1990 | |
| JP | 03019703 A | * | 1/1991 | |
| JP | 07214406 A | * | 8/1995 | |
| JP | 2000052114 A | * | 2/2000 | |
| JP | 2002137111 A | * | 5/2002 | |
| WO | 96/10962 | 4/1996 | | |
| WO | 2004/082490 | 9/2004 | | |
| WO | WO 2008020828 A2 | * | 2/2008 | ........... B23B 31/005 |
| WO | 2012/138337 | 10/2012 | | |
| WO | 2012138338 | 10/2012 | | |

OTHER PUBLICATIONS

International Preliminary Report on Patentability and Written Opinion, dated Oct. 8, 2013, in corresponding International Application No. PCT/US2011/031512.

International Search Report, dated Jan. 4, 2012, in related International Application No. PCT/US2011/031512.

International Preliminary Report on Patentability and Written Opinion, dated Oct. 8, 2013, in related International Application No. PCT/US2011/031505.

International Search Report, dated Feb. 28, 2012, in related International Application No. PCT/US2011/031505.

U.S. Appl. No. 15/225,043, filed Aug. 1, 2016.

* cited by examiner

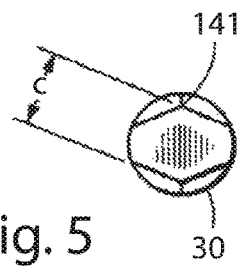
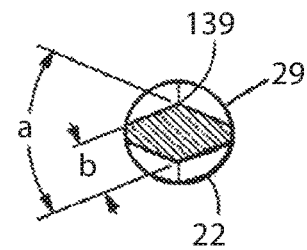
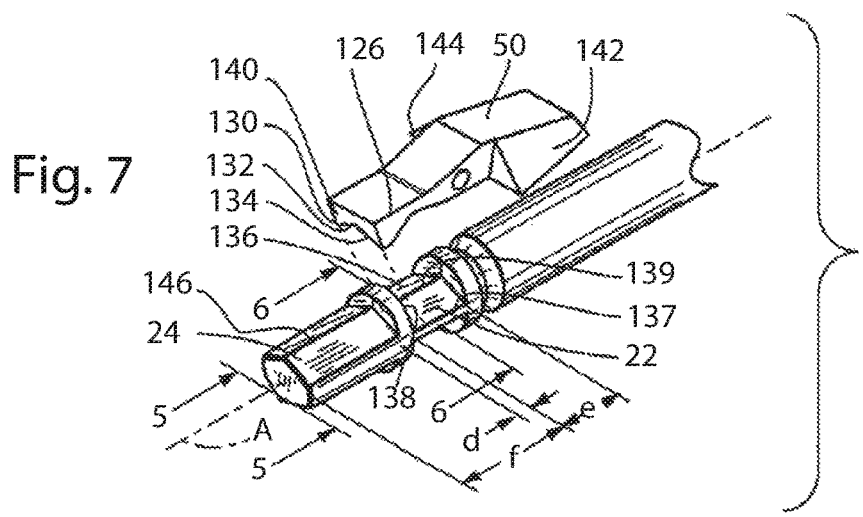
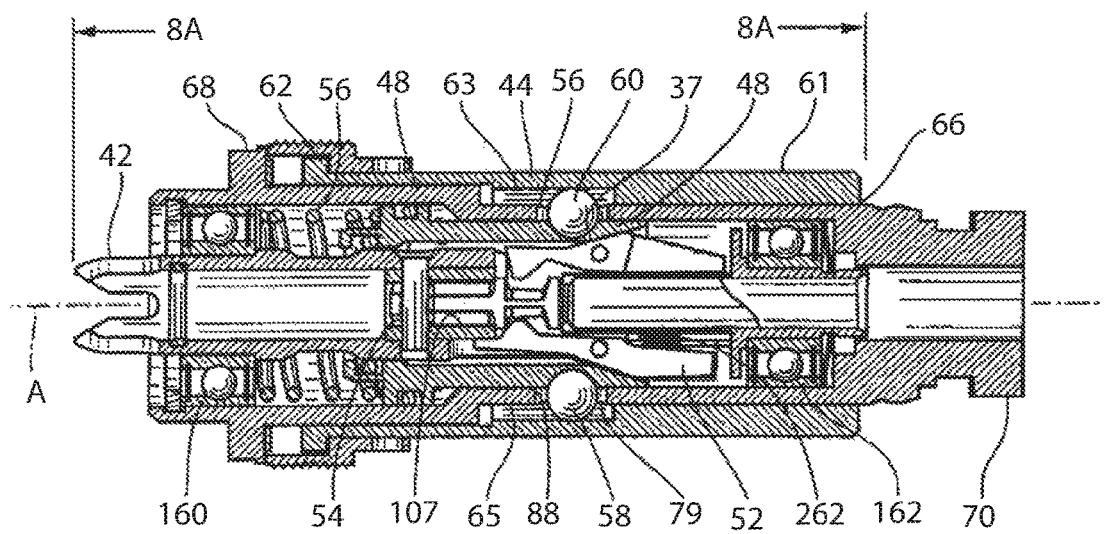

SURGICAL DRILL INSTRUMENT WITH MOTOR AND LOCKING MECHANISM TO RECEIVE AN ATTACHMENT AND A CUTTING BURR

CROSS REFERENCE TO RELATED APPLICATION

This application is a continuation of U.S. application Ser. No. 14/833,401, filed Aug. 24, 2015, entitled "SURGICAL DRILL INSTRUMENT WITH MOTOR AND LOCKING MECHANISM TO RECEIVE AN ATTACHMENT AND A CUTTING BURR," which is a continuation of U.S. application Ser. No. 14/456,383, filed Aug. 11, 2014, entitled "SURGICAL DRILL INSTRUMENT WITH MOTOR AND LOCKING MECHANISM TO RECEIVE AN ATTACHMENT AND A CUTTING BURR," which is a continuation of U.S. application Ser. No. 13/082,029, filed Apr. 7, 2011, entitled "SURGICAL DRILL INSTRUMENT WITH MOTOR AND LOCKING MECHANISM TO RECEIVE AN ATTACHMENT AND A CUTTING BURR." The disclosures of which are incorporated herein by referenced in their entirety. The subject matter described in this application is related to subject matter disclosed in the following commonly assigned application: U.S. patent application Ser. No. 13/082,016, filed on Apr. 7, 2011, entitled "CUTTING BURR SHANK CONFIGURATION," which is incorporated herein by reference in its entirety.

BACKGROUND

Surgical drilling instruments may include two releasably attached modular components, e.g., a motor/locking mechanism and an attachment, where the attachment attaches to the end of the locking mechanism. These modular components serve to receive and drive a high speed cutting burr that fits through the attachment and is engaged by the locking mechanism for high speed drilling, for example, at 80,000 to 90,000 R.P.M. The motor/locking mechanism may accept different kinds and sizes of cutting burrs or bits and different kinds and sizes of attachments.

The attachment of the cutting burr or bit to the motor/locking mechanism of may be difficult to use. For example, to install the cutting burr into some surgical drills, the operator may need to attach the attachment to the locking mechanism, position a lever on the surgical drill, and then insert the cutting burr into the attachment. To remove the cutting burr, the tasks may be reversed by placing the lever into a raised position and removing the cutting burr. The process is then repeated to insert the next cutting burr. In the above process, an operator may encounter problems if the lever position is moved from the raise position before the cutting burr is inserted.

Other quick release coupling mechanisms include the use of a posterior and an anterior Double D collet. The collet housing is mounted in line with the instrument's housing and is rotatable to two positions. Rotation of the collet housing to first, locking position causes a ball to ride in a helical slot for positioning a closure sleeve to urge the locking ball into the annular groove formed in the distal end of the cutting burr to lock the cutting burr in place. For removal of the cutting burr the reverse procedure is performed. For example, the collet housing is rotated to a second position causing the closure sleeve to move away from the ball and allow it to release itself from the annular groove in the cutting burr and allowing the cutting burr to be remove. To insert another cutting burr, the cutting burr is inserted and the collet housing is rotated back to the locking position. The cutting burr cannot be inserted if the collet housing is in the locked position.

Thus, quick release coupling mechanisms pose difficulties in their use, especially during operations where a cutting burr may only be useable for less than 10 minutes, and may have to be changed several times during a surgical procedure. As such, the efficiency, ease and timeliness of the cutting burr changing procedure may affect the surgical procedure.

SUMMARY

Disclosed herein is surgical apparatus having a locking mechanism that receives a cutting burr having diamond-shaped portions formed at a proximal end of the cutting burr. The locking mechanism may include a motor-driven spindle, to which a locking pawl and a detent pawl are pivotally attached. The locking pawl may serve to lock the cutting burr in place and the detent pawl may hold the cutting burr in place when locking mechanism is in a loading position, and may serve to reduce the likelihood of the cutting burr inadvertently falling out of the surgical drill instrument.

In some implementations, a proximal diamond-shaped portion of the cutting burr may be formed as a six-sided (e.g., hexagonal) diamond configuration and include a perpendicular back end surface. Disposed axially from the diamond-shaped portion formed in the proximal end of the cutting burr is another diamond-shaped portion formed having a six-sided (e.g., hexagonal) diamond shape surface that mates with a complementary surface of the locking pawl of the locking mechanism. In an aspect, the attachment of the cutting burr within the locking mechanism is such that is such that the cutting burr has substantially zero axial movement and runs substantially true when the surgical drill is in a running condition. In another aspect, insertion of a cutting burr having a different design will cause the surgical drilling instrument to vibrate, thus alerting the user that the wrong or incompatible cutting burr is being used.

According to some implementations, the locking pawl may include an increased mass portion at an end opposite of an engagement end of the locking pawl that contacts the axially disposed diamond-shaped portion. During use, a centrifugal force is applied to the mass end causing the locking pawl to pivot and apply greater pressure on the axially disposed diamond-shaped portion of the cutting burr, thus providing enhanced locking thereof within the surgical drilling instrument.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary is better understood when read in conjunction with the appended drawings. For the purposes of illustration, there is shown in the drawings exemplary implementations; however, these implementations are not limited to the specific methods and instrumentalities disclosed. In the drawings:

FIG. 5 is an end view of the cutting burr illustrated in FIG. 7 illustrating the outermost diamond-shaped portion;

FIG. 6 is a sectional view taken along lines 6-6 of FIG. 7 illustrating the innermost diamond-shaped portion;

FIG. 7 is a fragmentary perspective and exploded view illustrating the proximal end of the cutting burr and the locking pawl the disclosure;

FIG. 8 is a sectional view of the locking mechanism illustrating the loading position the disclosure;

DETAILED DESCRIPTION

While the description contained in the present disclosure uses certain names for certain instruments and components, the industry may have other names for these same items, and as it is understood by those skilled in this art and to avoid confusion, the following examples are presented herein without limitation. The surgical drilling instrument may be referred to as the cutter, motor, drill and the like; the cutting burr may be referred to as fluted ball, diamond ball, twist drill, router and the like; and the attachment may be referred to as angle attachment, minimally invasive attachment, controlled depth attachment, speed reducer and the like. The cutter, as used in this description may also refer to the motor and locking mechanism.

Overview of the Surgical Drill Instrument

High speed surgical drills are increasingly being used by surgeons when performing delicate bone dissection in areas such as the cervical and lumbar spine. Such surgical drills operate at very high R.P.M., and are able to rotationally drive multiple types of attachments and cutting burrs. As will be described below, the surgical drill instrument of the present disclosure receives a cutting burr having a shank that defines two diamond-shaped portions. The diamond-shaped portions provide for ease of insertion and removal of the cutting burr to and from the surgical drill. The diamond-shaped portions also provide for axial locking of the cutting burr and enable the surgical drill to direct higher levels of torque to the cutting burr during surgical procedures.

Figure 1A:
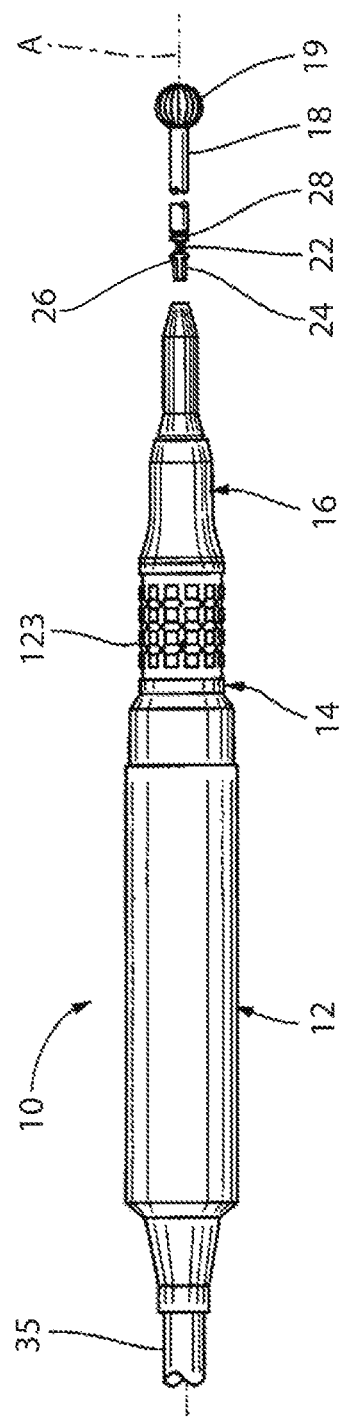
FIG. 1A is a front view illustrating the surgical drilling instrument and cutting burr and a perspective and sectional view of the locking instrument and the attachment the disclosure.
Figure 1B:
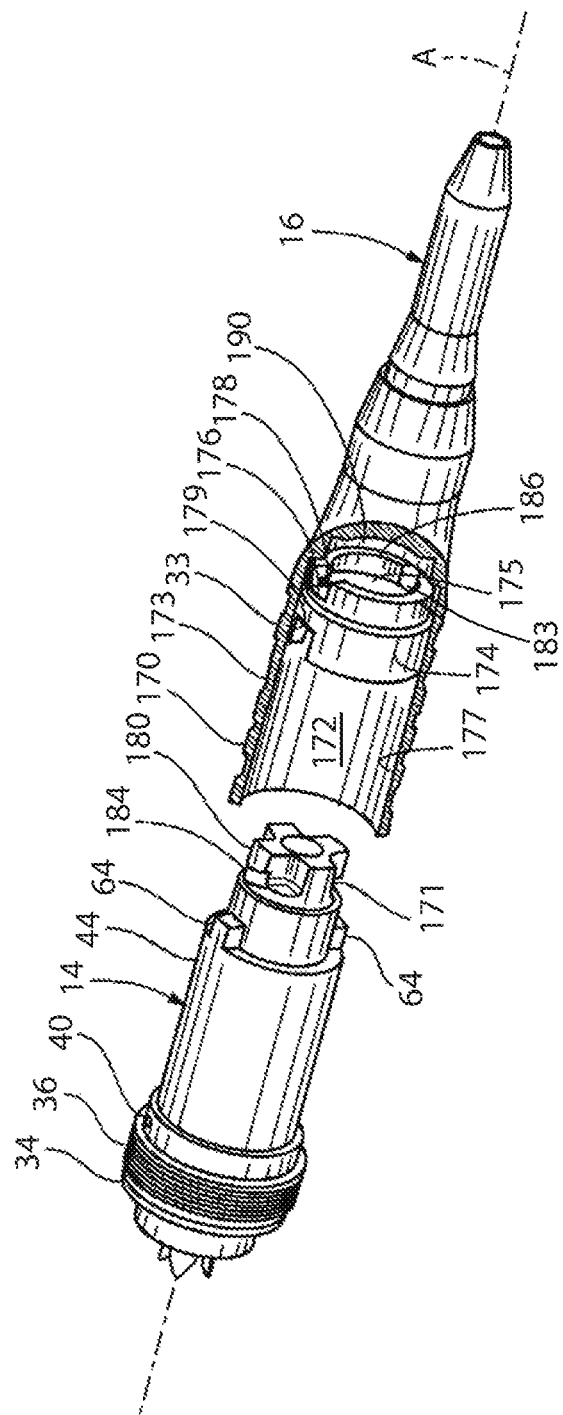
FIG. 1B is a perspective view partially in section illustrating the surgical drilling instrument and cutting burr and a perspective and sectional view of the locking instrument and the attachment the disclosure.

Referring now to FIGS. 1A and 1B, the surgical drill instrument is generally illustrated by reference numeral 10 and comprises electric a motor 12, a locking mechanism 14, an attachment 16, a cutting burr 18 and a cutting bit 19. The attachment 16 may include an outer case portion 33 that fits over the locking mechanism 14 and defines therewith a smooth cylindrical portion and transitional tapering portion of the instrument that provides a good line-of-sight for the surgeon. The cutting bit 19 is disposed on the distal end of a shank 20.

As shown, electric cable 35 extends from the motor 12 to deliver power to the motor 12 either via a commercially available electric outlet or console which may include a foot pedal control (not shown), of the type available from the assignee, The Anspach Effort, Inc. of Palm Beach Gardens, Fla. The motor 12 may drive a spindle 42, the cutting burr 18, the locking mechanism 14 and the attachment 16. As details of the motor 12 and console are known in the art, the description thereof is omitted. The motor may include a control mounted to the motor's housing, such as a control lever, that allows the operator to turn the motor on and off or control the speed thereof. The motor may also be a pneumatic motor and the like. The materials used for the surgical drill instrument, attachment and cutting burr are commercially available material typically used for the construction of medical equipment and of the type that may be suitable to be autoclaved. Features of the surgical drill 10 and cutting burr 18 will now be described.

Diamond-Shaped Portions 22 and 24

As shown in FIGS. 1, 5 and 6, the shank 20 may have formed at a proximal end thereof, two diamond-shaped portions, 22 and 24. The shank 20 of the cutting burr 18 may be cylindrically shaped, as shown, or may take other shapes, such as polygonal in cross section, and the like. The diamond-shaped portion 22 is formed on the innermost of the proximal end of the shank 20 and may be milled into the diamond-shaped configuration. The diamond-shaped portion 22 may include a tapered fore wall 28 having a taper fairing from an inner diameter of the shank 20 to the outer diameter of the shank 20.

The diamond-shaped portion 24 may be milled at the outermost of the proximal end of shank 20 and may include diamond-shaped configuration (e.g., a key; see, FIG. 5) and a perpendicular aft wall 26. The diamond-shaped portion 24 may be keyed to be inserted into a key slot 107 of the surgical drill 10. The facets of the diamond-shaped portion 24 provide positive engagement surfaces in both clockwise and counter-clockwise rotational directions with the drive recess. For example, some surgical drills provide bi-directional rotation, allowing the surgeon to selectively reverse rotation for various surgical techniques. In conventional designs, there may be rotational play between a bit end and a drive recess. However, the symmetrical diamond facets of the diamond-shaped portion 24 provide substantial drive surfaces in either direction, and thus a sufficient cross-sectional dimension to meet strength and reliability requirements needed for high-speed, large force surgical applications. In addition, the diamond-shaped portion 24 also provides for a unidirectional backward compatibility with older drill instruments 10. While the cutting burr 18 is described as having two diamond-shaped portions, it is noted that other polygon profiles are contemplated by the present disclosure, such as a parallelogram, an octagon, a star shaped pattern, etc. While the diamond-shaped portions 22 and 24 are described as being "diamond-shaped," it is noted that such terminology is intended to encompass any six-sided (hexagon) shape having a cross-section with flat edges that meet at a six vertices, curved edges that meet at six points, or some combination of both to form the six sides. The flat and curved edges, and combinations thereof, may be applied to other polygon shapes having different numbers of sides.

FIGS. 5 and 6 are sectional views of the diamond-shaped portions 22 and 24. The two diamond-shaped portions may be different in size, where the diamond-shaped portion 24 is larger than the diamond-shaped portion 22. The apexes 139 and 146 of the diamond-shaped portions 22 and 24 may fall below the outer diameter of the shank 20, and both diamond-shaped portions 22 and 24 may be in axial alignment with each other and oriented in parallel relationship. In some implementations, the diamond-shaped portion 24 and the diamond-shaped portion 22 may be the same size, or the diamond-shaped portion 22 may be larger than the diamond-shaped portion 24. In the various configurations, the apexes 139 and 146 of diamond-shaped portions 24 and 22, respectively, are along a same line and in a same plane as the center line A. Additionally, the dimensions of the diamond-shaped portions 22 and 24 are listed in degrees (°) and inches (') and are substantially as follows:

The angle of the facets of the six-sided diamond in the diamond-shaped portion 22–a=47°;

The width of the facets of the six-sided diamond in the diamond-shaped portion 22–b=0.046";

The width of the facets of the six-sided diamond in the diamond-shaped portion 24–c=0.065";

The width of the shank 16 at the space between diamond-shaped portions 22 and 24–d=0.029";

The length of the diamond-shaped portion 22–e=0.068"; and

The length between the proximal end and the back wall of diamond-shaped portion 22–f=0.149".

Figure 4:
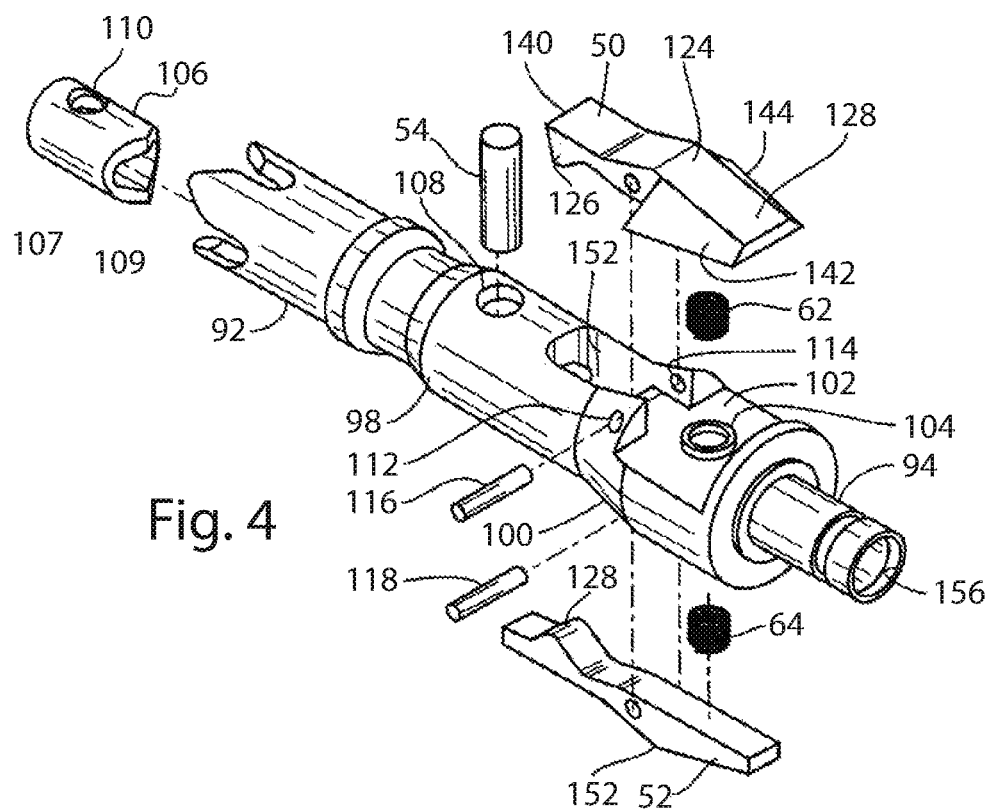
FIG. 4 is a perspective and exploded view of the drive spindle of the locking mechanism illustrating the locking and detent pawls, the cutting burr stop pin and the spindle insert the disclosure.

As will be described below, the diamond-shaped portion 22 is provided as an abutment surface for axial locking by a retractable locking pawl 50 (FIGS. 4 and 7) of the surgical drill 10, whereas rotational forces may be incident upon the diamond-shaped portion 24. The position and orientation of the diamond-shaped portion 22 is such that the locking pawl 50 may lock the cutting burr 18 in the surgical cutting instrument as the diamond-shaped portion 22 mates with a complementary surface formed on the engagement end of the locking pawl 50.

Locking Mechanism 14

Aspects of the locking mechanism 14 are generally illustrated in FIGS. 1, 3, 3A, 3B, 3C, 3D, 8, 8A and 9. The locking mechanism 14 receives the cutting burr 18, and may include a motor driven spindle 42 that carries the locking pawl 50 and a detent pawl 52. In a loading position of the locking mechanism 14, an inner sleeve of the locking mechanism 14 engages the spindle 42 to brake the motor 12 and spindle 42. The inner sleeve engages the locking pawl 50 to hold it in a position that prevents it from engaging the diamond-shaped portion 22 of the cutting burr 18. Meanwhile, the detent pawl 52 is biased by a spring 64 such that an engagement end of the detent pawl 52 comes into contact with the diamond-shaped portion 22 with sufficient force that will allow the cutting burr 18 to be moved in and out, but yet reduces the likelihood that the cutting burr 18 may inadvertently fall out when the surgical cutting instrument is in the loading position.

With the cutting burr 18 inserted into the locking mechanism 14, the locking mechanism may be changed from the loading position to the running position by an outer sleeve that is rotated to force the inner sleeve to move axially in a position to disengage the spindle 42 and locking pawl 50, thus allowing the locking pawl 50 to deploy and engage the diamond-shaped portion 22 of the cutting burr 18 to lock it into position. As noted above, the locking pawl 50 serves to lock the cutting burr 19 in place by engaging the diamond-shaped portion 22, substantially reducing axial movement. In the running position, the surgical drill 10 and cutting burr 18 are ready for use in a surgical procedure.

The details of the locking mechanism 14 will now be described. FIG. 1B illustrates that the locking mechanism 14 may include a retainer ring 34 mounted on the proximate end that threadably engages, via threads 36 formed on the outer periphery surface of retainer ring 34, complementary threads (not shown) formed in the housing of electric motor 12 so as to be coupled thereto. Spanner engaging apertures 40 may be formed on the smaller diameter portion of retainer ring 34 to allow a spanner wrench to secure the locking mechanism 14 to motor 12. The distal end of attachment 16, when assembled, may encapsulate the locking mechanism 14 and defines with the motor, a smooth cylindrical shaped instrument that is tapered that serves as a handle while providing an excellent line of view for the surgeon to use in a medical procedure. The locking mechanism, spindle, attachment and the operation are described below.

Figure 3:
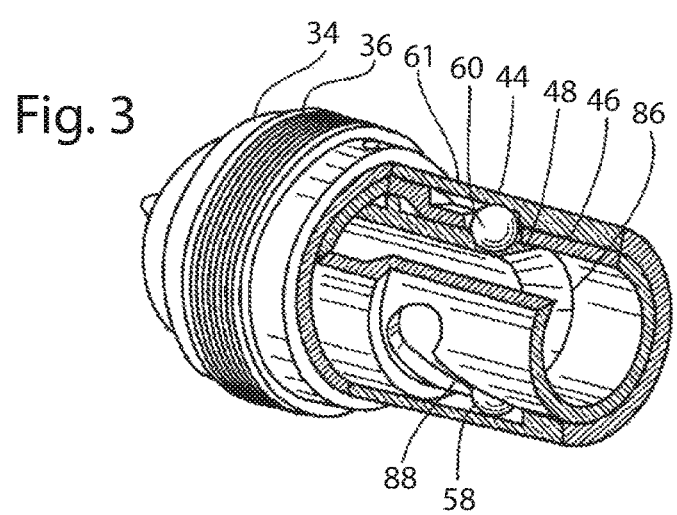
FIG. 3 is a fragmentary view in perspective and partly in section of the locking mechanism illustrating the cutter lock housing (intermediate sleeve), locking actuator (outer sleeve) and outer brake mount (inner sleeve) the disclosure.
Figure 3A:
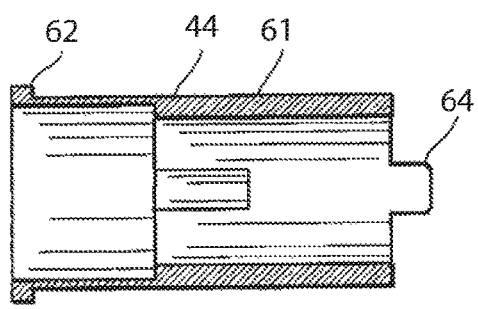
FIG. 3A is a sectional view illustrating the locking actuator (outer sleeve) of the locking mechanism the disclosure depicted in FIG. 3.
Figure 3B:
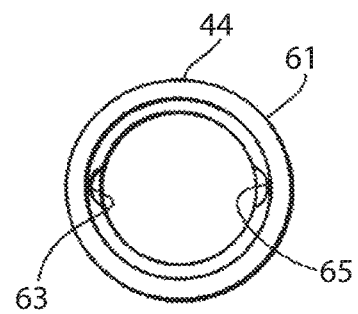
FIG. 3B is an end view of the locking actuator depicted FIG. 3A.
Figure 3C:
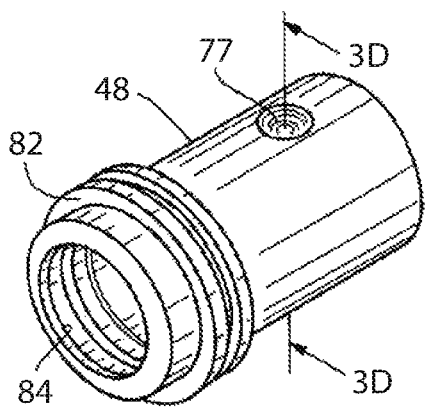
FIG. 3C is a perspective view of the outer brake mount (inner sleeve) of the locking mechanism the disclosure depicted in FIG. 3.
Figure 3D:
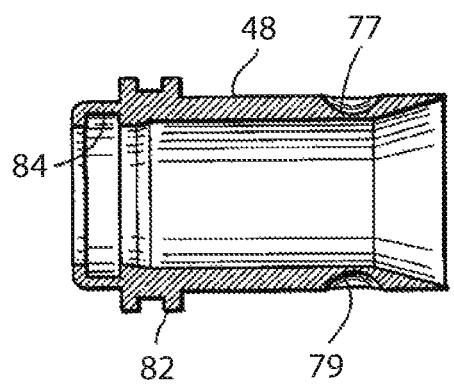
FIG. 3D is a sectional view of the outer brake mount depicted in FIG. 3C.

As shown in FIG. 3, the locking mechanism 14 may include three concentric sleeves, 44, 46 and 48, the spindle 42, the locking pawl 50, the detent pawl 52, a locating dowel pin 54, a coil spring 56, a pair of driving balls 58 and 60, and pawl springs 262 and 264. The motor driven spindle 42 is mounted about axis A for rotary motion. Sleeves 44, 46 and 48 are concentrically disposed relative to spindle 42 and all are coaxially disposed around center line A. The locking pawl 50 and the detent pawl 52 are pivotally mounted on spindle 42 and rotate therewith.

The three concentric sleeves 44, 46 and 48 may provide several functions, as will be explained below. The outer sleeve 44 may define a lock actuator which is fixed relative to the spindle 42, and has a small circumferential movement for the purpose of positioning balls 58 and 60 to ultimately position inner sleeve 48 linearly. The outer sleeve 44 may include an outer casing portion 61, outwardly projecting flange portion 62 extending radially outwardly from the aft end, a pair of projections or tabs 64 extending axially from the fore end thereof and diametrically disposed hemispherical slots 63 and 65. The intermediate sleeve 46 that defines the cutter lock housing, is fixed relative to spindle 42 and outer sleeve (lock actuator) 44 and may be formed from a main hollow cylindrical member 66 having a radial outward flange portion 68 disposed on the aft end and an attachment portion 70 disposed on the fore end and a pair of diametrically opposed cam slots 86 and 88 formed intermediate the ends thereof.

As shown in FIG. 8, a flange portion 62 and a flange portion 68 are spaced from each other defining an annular space 72 providing sufficient space for sleeve 44 to rotate. The inner sleeve (outer brake) 48 defines a brake, and locking pawl 50 engagement and disengagement member is fixed relative the spindle 42 and is movable rectilinearly. The inner sleeve 48 may include a main body portion 78, a tapered end portion 80 and spaced O-ring inner and outer retaining flanges 82 and 84 for supporting O-rings 83 and 85, which serve to seal the motor from foreign matter and diametrically opposed apertures 77 and 79. A portion of balls 58 and 60 fit into apertures 77 and 79, respectively, hemispherical slots 63, 65, respectively and through cam slots 86 and 88, respectively, and serve to move inner sleeve 48 linearly. When the outer sleeve 44 is rotated a portion of balls 58 and 60 bears against it so that the hemispherical slots in the outer sleeve 44 rotate the captured balls in a circumferential direction.

A portion of balls 58 and 60 pass through cam slots 86 and 88, respectively, that are contoured to define a particular linear movement, and a portion of balls 58 and 60, extend into apertures 77 and 79, respectively, such that the contour of clam slots 86 and 88 serve to cause the balls to move inner sleeve 48 axially thereby effectuating braking and un-braking of the spindle 42 and motor 12 and the engagement and disengagement of the locking pawl 50. This movement may provide a braking function, but it also allows the locking pawl 50 to pass through the spindle 42 wall and engage the diamond-shaped portion 22 of cutting burr 18. A coil spring 56 is disposed between the ball bearing 90 and the O-ring retaining flange 85 for biasing inner sleeve 48 toward the fore end of locking mechanism. When sleeve 48 is rotated in one direction, the spring 56 compresses and in the opposite direction coil spring 56 becomes uncompressed.

Spindle 42

The spindle 42 is generally illustrated in FIGS. 4, 8, 8A and 9. As shown, the locking pawl 50 and detent pawl 52 are pivotally mounted to the spindle 42 and rotate therewith during operation of the surgical drill instrument 10. The locking pawl 50 may include an increased mass end 128 such that rotation of the spindle 42 during use applies a centrifugal force to the mass end 128. The increased force on the mass end 128 causes the locking pawl 50 to pivot and apply greater pressure on the diamond-shaped portion 22 of the cutting burr 18, thus providing enhanced locking thereof within the surgical drilling instrument 10.

Further, in accordance with some implementations, when the cutting burr 18 is inserted into the surgical drilling instrument 10, the spindle 42, the locking pawl 50 and the detent pawl 52 are deployed at a predetermined alignment such that they are rotationally balanced and provide a substantially vibration-free operation. However, if a different (e.g., less compatible) cutting burr is inserted, the spindle 42, the locking pawl 50 and the detent pawl 52 may not attain the predetermined alignment, thus the surgical drilling instrument 10 may vibrate during use to warn an operator of the potential incompatibility.

The spindle 42 has a drive attachment end 92 at the aft end connected to the drive shaft (not shown) of the motor 12 and being driven thereby, and an attachment portion 94 at the fore end thereof for attaching to the attachment 16. Bearings 160 and 162 disposed inside the fixed sleeve 46 serve to support spindle 42 for rotary motion. The main body portion 96 of spindle 42 is a cylindrical and hollow and may include a reduced diameter portion 98 formed intermediate the ends thereof, a conical shaped portion 100 defining a braking surface formed intermediate the ends thereof, opposing flattened portions 102, opposing spring retainer recesses 104 and a plurality of apertures. The spindle 42 may include an insert 106 that is milled to define a diamond-shaped key slot 107 that is rigidly supported in the cavity of spindle 42 and a pointed shaped inlet end 109 serves to facilitate the alignment and insertion of the cutting burr 18.

Drilled opposing holes 108 align with drilled opposing holes 110 formed in insert 106 for receiving dowel pin 54 which serves to locate the cutting burr when inserted into the spindle 42 and when the end thereof abuts there against. The opposing drilled holes 112 and 114 formed in the conical portion of spindle 42 serves to support the axles 116 and 118, respectively that pass through the holes 120 and 122 formed in the locking pawl 50 and detent pawl 52, respectively to provide pivotal support.

Figure 8A:
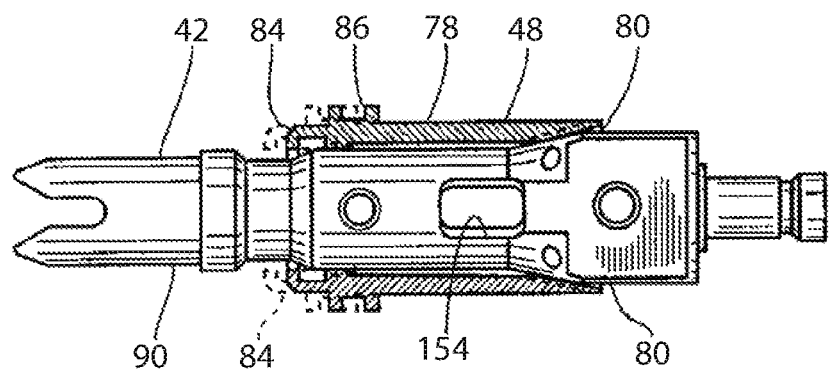
FIG. 8A is a fragmentary elevated view partly in section with certain components removed to illustrate the braking and un-braking conditions provided to assure braking the spindle and motor during loading and running conditions of this inventive surgical drilling instrument.
Figure 9:
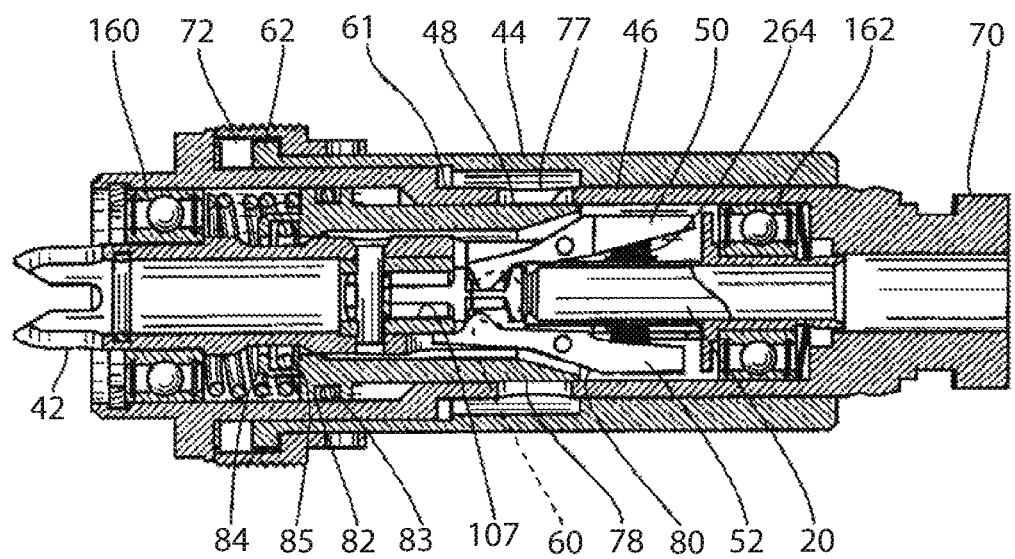
FIG. 9 is a sectional view of the locking mechanism the disclosure illustrating the running position.

As best shown in FIGS. 8, 8A and 9 the locking pawl 50 may include the lever arm 124, cutting burr engagement end 126 and an increased mass end 128. The spring 262 fits into retainer 104 and bears against the underside of the increased mass portion of lever 124 and biases engagement end 126 toward the center line A causing the locking pawl to pivot about axle 116 in a counterclockwise direction.

The detent pawl 52 is similarly constructed, but may not include the increased mass end. The engagement end 129 of detent pawl 52 is contoured differently from the engagement end 126 of the locking pawl 50 and is contoured in a generally hill shape and is sized to partially fit into the diamond-shaped portion in the cutting burr on the opposite side of the engagement end 126. The spring 264 biases the lever 152 to rotate in a clockwise direction about axle 118 to place the hill shaped portion into the diamond-shaped portion with sufficient force that will allow the cutting burr to be moved in and out when the cutting burr is inserted and removed and yet prevent the cutting burr from inadvertently falling out when the surgical cutting instrument is in the loading position. As will be described in more detail hereinbelow, spindle 42 may include an enlarged cut out portion 154 that extends through the spindle 42 and allows the locking pawl 50 to engage the cutting burr via diamond-shaped portion 22 and provides a passageway for detent pawl 52 to partially fit into diamond-shaped portion 22 of the cutting burr when inserted into the central bore 156.

FIG. 7 illustrates the contour on the engagement portion of locking pawl 50 and the wing shaped portions 142 and 144 that increase the mass 128 at the end of the locking pawl 50. The engagement end 126 may be contoured in a V-shape with inner surfaces 132 and 134 that fit against the facets 136 and 137 of the diamond-shaped portion formed in the cutting burr. A back face 130 at the end 140 of the locking pawl 50 may abut against the inner face 138 at the aft end of the diamond-shaped portion 24 and the configuration of the engagement portion. Owing to the design of the engagement end 126 of locking pawl 50 and the proximate end of the cutting burr 18, the cutting burr 18 is prevented from displacing axially when running. In other words, there is substantially no axial play in the surgical cutting instrument, which provides for precision cutting, shaping and the like. In operation, the wings 142 and 144 extending from the side walls of locking pawl 50 at the mass end 129 add pressure to the engagement end 126 when running because of the centrifugal force created by the rotation of the spindle 42.

Attachment 16

Figure 2:
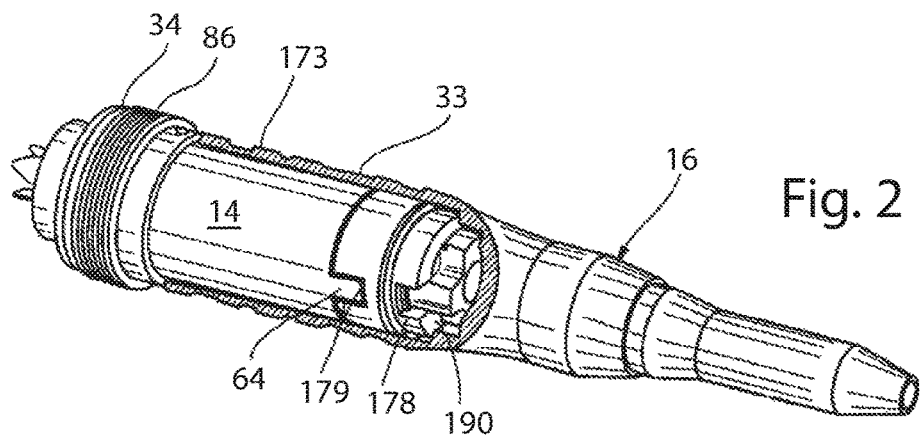
FIG. 2 is a perspective view partly in section illustrating the attachment mechanism for attaching the attachment to the locking mechanism the disclosure.

The attachment 16 is generally illustrated in FIGS. 1 and 2, and may include a main housing 170 having a cut-out grooved upper surface 173 that serves as a handle and control for the surgeon or operator for placing the surgical drilling instrument in the loading and running positions. The attachment 16 may include a central bore to allow the cutting burr to pass there through and a disk 174 laterally mounted in a central cavity 172 of the attachment 16 and is formed with judiciously spaced slots 178 and 179 for deploying the surgical instrument in the loading and running position as will be described in detail herein below. The central cavity 172 in main housing 170 is sized to fit over the sleeve 44 and abut against the retainer ring 34 to define a smooth outer surface of the instruments, saved for the groove portion 173.

Disk 174 is fixedly secured in central cavity 172 and may include a central bore 175 and a pair of the back-to-back axial cut outs 176 and 178.

To connect attachment 16 to the locking mechanism 14, the end of locking member is inserted into central cavity 172 and any two of the cog gears 180 fit through and pass cut out 178 so that the surface 184 at the aft end extends behind the end 186 of hollow disk 174 and fit in the annular space 190. Also, projections or lugs 64 extending from locking mechanism 14 fit into cutout 176, as shown in FIG. 2. The outer surface of sleeve 44 snugly fits against the inner surface of ring 174 so as to be held in position or alternatively, a resilient member like an O-ring 183 can be mounted on the inner surface of the ring 174 adjacent to cut out 178. The above places the locking mechanism 14 surgical drilling instrument 10 in the loading position. To change the locking mechanism 14 to the running position, the attachment 16 is rotated via the main housing 170 causing the cog wheel 171 and the cog gear 180 to rotate in the space 190 adjacent to the end of the ring 174 and by virtue of the connection of lugs 64 connected to actuator 16, the locking mechanism will be placed in the running position.

Thus, with the structure and interoperation of the various components of the surgical drilling instrument now described, the operation and use of the surgical drilling instrument will now be introduced.

Operation of the Surgical Drilling Instrument 10

During a surgical procedure, a particular attachment 16 and cutting burr 18 may be selected by e.g., a surgeon or operator to be used with the cutter. The operator may first attach the attachment 16 to the locking mechanism 14 by inserting the attachment 16 so that the main housing 170 of attachment 16 abuts against and aligns with the retainer ring 34. The cog wheel 171 and cog gear members 180 will align with cutout 178 and pass therethrough until the aft end fits into the annular space 190. Also the lugs 64 will align with and fit into cutout 176. (See FIG. 2).

The cutting burr 18 is then inserted through the fore end passing the central cavity in spindle 42 so that the diamond-shaped portion 24 aligns with and fits into the diamond-shaped key slot 107 formed in spindle 42 or insert 106. This constitutes the loading position as shown in FIG. 8. The locking mechanism 14 is held in position in the attachment by virtue of a tight fit or by the aid of the resilient ring 177. In the loading position (FIGS. 8 and 8A), sleeve 48 is urged by coil spring 56 toward the fore end so that the tapered surface 80 bears against the conical surface 100 of spindle 42 serving to lock the spindle 42 and brake the motor and preventing them from rotating. The sleeve 48 bears against locking pawl 50 and holds it in a disengagement position so as to prevent it from engaging cutting burr 18.

When the cutting burr 18 is completely inserted, the end thereof will abut against dowel pin 54 establishing the distance the cutting burr projects beyond the attachment 16. The detent pawl 52 that is pivotally connected to spindle 42 is urged by spring 62 to project through the cutout 154 in spindle 42 to partially fit into diamond-shaped portion 22. The spring rate of spring 62 is selected to assure that the detent pawl 52 has sufficient force to prevent the cutting burr 18 from falling out of the cutter inadvertently and yet, permit the removal of the cutting burr without requiring a great deal of force. The surface 129 of detent pawl 52 is contoured to facilitate the removal and insertion of the cutting burr 18.

To place the cutter in the running position, the main housing 170 of attachment 16 is rotated causing sleeve 48, in turn, to move axially toward the rear end of locking mechanism 14 (FIGS. 9 and 8A). This is occasioned by positioning balls 58 and 59 as will be immediately explained. As mentioned above, a portion of balls 58 and 60 fit into hemispherical slots 63 and 65 of the outer sleeve 44, extend through cam slots 86 and 88 of sleeve 46 and fit into apertures 77 and 79 of sleeve 48. Rotation of the outer sleeve 44, say 90 degrees, by virtue of rotating attachment 16, causes the balls 58 and 60 to travel in cam slots 86 and 88 formed in sleeve 46.

The ball portions fitting into apertures 77 and 79 cause the sleeve 48 to move axially against the force of spring 56 toward the rear end of the locking mechanism 14. As shown in FIGS. 9 and 8A, when sleeve 48 moves rearward it unlocks both locking pawl 50 and spindle 42 (see the dash lines in FIG. 8A). This movement of sleeve 48 allows the engagement end 126 of locking pawl 50 to pass through the aperture 154 in spindle 42 and engage a portion of the six-sided diamond (top portion as viewed in FIG. 9) and lock cutting burr 18 in place.

In accordance with some implementations, the cutting burr may be installed when the locking mechanism 14 is in the loading and running position. For example, if during a surgical procedure the original cutting burr becomes worn out and needs to be replaced, the locking mechanism 14 may be placed in the loading position to allow the cutting burr 18 to be removed. As such, the balls 58 and 60 are re-positioned to the original position allowing spring 56 to force sleeve 48 to move toward the front of the locking mechanism 14. This locks the spindle 42 and retracts the locking pawl 50, as noted above. If the locking mechanism 14 is positioned from the loading position to the running position prior to inserting the replacement cutting burr 18, locking pawl 50 is returned to the locking position to engage the diamond-shaped portion 22 of the cutting burr.

Notwithstanding this condition, the cutting burr 18 may still be inserted even though the locking mechanism is in the running position. In particular, as the cutting burr 18 is inserted and forced inwardly toward the key slot 107 in spindle 42, the outer diameter at the proximal end of the cutting burr 18 will abut the contoured end of the engagement end 126 of the locking pawl 50, forcing it upwards against the force of spring 62. The spring rate of the spring 62 may be a value that will allow the cutting burr 18 to proceed to the dowel pin 54 within the key slot 107. As such, as the cutting burr 18 proceeds to the dowel pin 54, the spring 62 will cause the engagement end 126 of the locking pawl 50 to engage the diamond shape portion 22, thus locking cutting burr 18 in position. As such, the surgical drilling instrument 10 is now ready for use in the medical procedure.

Thus, as described herein, the apparatus of the present disclosure provides for a locking mechanism and attachment that are relatively simple to manufacture and that are user friendly. The locking mechanism and attachment provide for relatively easy insertion and removal of the cutting burr. The diamond-shaped portions limit axial play of the cutting burr and provide a substantial surface area for driving the cutting burr with higher torque from surgical drilling instrument motor.

While particular aspects of the present subject matter described herein have been shown and described, it will be apparent to those skilled in the art that, based on the teachings herein, changes and modifications may be made without departing from the subject matter described herein and its broader aspects and, therefore, the appended claims are to encompass within their scope all such changes and modifications as are within the true spirit and scope of the subject matter described herein.

What is claimed:

1. A surgical drill, comprising:
a cutting burr including a shank defining a first six-sided portion and a second six-sided portion,
a spindle rotatable about a central axis, the spindle defining a cylindrical main body, the main body including a reduced diameter portion, opposing flattened portions defining bearing surfaces extending parallel to the central axis, and a conical shaped portion between the reduced diameter portion and the opposing flattened portions, the spindle further defining a keyed slot adapted to receive the first six-sided portion of the cutting burr;
a locking mechanism-releasably mounted to the spindle and comprising a plurality of concentrically disposed sleeves;
a detent pawl that contacts the second six-sided portion of the cutting burr at a predetermined force such that the cutting burr is movable in an axial direction while retaining the cutting burr within the surgical drill when the locking mechanism is in a loading position;
a locking pawl pivotally attached to the spindle and having an engagement end adapted to engage adjacent surfaces of the second six-sided portion of the cutting burr received within the locking mechanism when the locking mechanism is in a running position; and
a motor for driving the spindle and the locking mechanism,
wherein the spindle includes a first and second aperture extending through the spindle at a location adjacent the opposing flattened portions, the first and second apertures sized and b configured to allow the detent and locking pawls to extend into the spindle and engage the cutting burr.

2. The surgical drill of claim 1, wherein the cutting burr comprises:
a shank portion defining the first six-sided portion at a proximal end and defining the second six-sided portion at a position that is axially spaced from the first six-sided portion, the first six-sided portion and the second six-sided portion comprising a first six-sided diamond-shaped portion and a second six-sided diamond-shaped portion, respectively,
wherein and the locking pawl engages the second six-sided diamond-shaped portion and the keyed slot comprises an complementary diamond-shaped portion adapted to receive the first six-sided diamond-shaped portion.

3. The surgical drill of claim 2, wherein the first six-sided diamond-shaped portion is larger than the second six-sided diamond-shaped portion.

4. The surgical drill of claim 2, wherein dimensions of each six-sided diamond-shaped portion are:
an angle of facets of the second six-sided diamond-shaped portion is approximately 47°;
a width of facets of the second six-sided diamond-shaped portion is approximately 0.046";
a width of facets of the first six-sided diamond-shaped portion is approximately 0.065";
a width of the shank portion at an axial space between the first six-sided diamond-shaped portion and the six-sided second diamond-shaped portion is approximately 0.029"; and
a length of the second six-sided diamond-shaped portion is approximately 0.068".

5. The surgical drill of claim 2, wherein respective apexes of the first six-sided diamond-shaped portion and the second six-sided diamond-shaped portion are along a same line and in a same plane as a center line defined by the spindle and the shank portion of the cutting burr when received by the spindle.

6. The surgical drill of claim 2, wherein two opposing sides of the first six-sided diamond-shaped and the second six-sided diamond-shaped portion each have a surface defined by a radius of curvature of the shank.

7. The surgical drill of claim 1,
wherein the locking pawl further comprises:
a pivotal lever pivotally mounted on the spindle, the engagement end on one end of the pivotal lever adapted to engage the second six-sided portion and a lever arm at an opposite end of the pivotal lever; and
a spring having one end bearing on one of the flattened portions of the spindle and another end of the spring bearing on the lever arm of the pivotal lever at a point to cause the lever to pivot for positioning the engagement end to engage and disengage the cutting burr,
wherein the detent pawl further comprises:
a pivotal lever pivotally mounted on the spindle, a mass end at one end of the pivot lever and a lever arm at an opposite end of the pivotal lever, and
a spring having one end bearing on an other one of the flattened portions of the spindle and another end of the spring bearing on the lever arm of the pivotal lever at a point to cause the lever to pivot for positioning the mass end to engage and disengage the cutting burr.

8. The surgical drill of claim 7, wherein the lever arm of the locking pawl further comprises a mass end, wherein rotation of the spindle causes a centrifugal force to be applied to the mass end causing the locking pawl to pivot, wherein the engagement end applies greater pressure on the second six-sided portion.

9. The surgical drill of claim 1, wherein the detent pawl and the locking pawl have different shapes, and
wherein when the cutting burr is inserted into the surgical drill, the detent pawl and the locking pawl have a predetermined alignment such that they are rotationally balanced when the spindle is rotated.

10. The surgical drill of claim 9, wherein if an incompatible cutting burr is inserted into the surgical drill, the detent pawl and the locking pawl do not achieve the predetermined alignment and the surgical drill vibrates when the spindle is rotated.

11. The surgical drill of claim 1, further comprising a dowel pin laterally extending in the spindle adapted to stop the cutting burr at a predetermined distance within the locking mechanism.

12. The surgical drill of claim 11, wherein the spindle further includes:
an insert having a cylindrical main body, the insert received within a central opening of the spindle, the insert defining the keyed slot for receiving a first six-sided portion of a cutting burr and having a pointed inlet end, wherein the pointed inlet end aligns the cutting burr during insertion,
wherein the dowel pin extends through the main body of the spindle and the insert to fix the location of the insert within the central opening of the spindle,
wherein an end of a cutting bur inserted into the spindle is abuts the dowel pin when the locking mechanism is in a running position.

13. The surgical drill of claim 1, wherein the plurality of concentrically disposed sleeves of the locking mechanism include an outer sleeve concentric to the spindle and coaxial therewith, an inner sleeve concentrically disposed to the outer sleeve and the spindle and coaxial therewith, and an intermediate sleeve concentrically disposed to the outer sleeve and the spindle and coaxial therewith.

14. The surgical drill of claim 13, wherein the inner sleeve of the locking mechanism is disposed adjacent to the locking pawl and movable to engage and disengage the locking pawl, and
  wherein the outer sleeve of the locking mechanism is rotatable in a circumferential direction to deploy the inner sleeve into one of the loading position and the running position.

15. The surgical drill of claim 13, further comprising a spring that acts on one end of the inner sleeve and biases the inner sleeve in a forward position,
  wherein the inner sleeve includes a tapered end that engages the conical portion of the spindle to brake the spindle when the locking mechanism is in the loading position.

16. A method of loading a cutting burr in a surgical drill, the surgical drill comprising a motor, a locking mechanism and a detachable attachment, cutting burr having a shank portion defining a first diamond-shaped portion and an axially spaced second diamond-shaped portion, the locking mechanism including a loading position and a running position, the method comprising:
  attaching the detachable attachment to the locking mechanism such that the locking mechanism is in the loading position;
  braking a spindle of the locking mechanism and holding a locking pawl of the locking mechanism in a detached position, the spindle having a cylindrical main body portion and a flattened portion defining a hearing surface that extends parallel to a central axis of the surgical drill, wherein when the locking pawl is in the detached position a portion of the locking pawl abuts the flattened portion;
  inserting the cutting burr into the surgical drill through an end of the detachable attachment and into the spindle of the locking mechanism such that the first diamond-shaped portion of the shank of the cutting burr fits into a defined key slot in the spindle and such that the second diamond-shaped portion is engaged by a detent pawl to hold the cutting burr in the surgical drill while providing a predetermined amount of axial movement of the cutting burr, the detent pawl extending into an aperture provided in the spindle to engage the second diamond-shaped portion, the aperture located between the keyed slot and the flattened portion; and
  placing the surgical drill in the running position by moving the detachable attachment to cease braking of the spindle and to cause the locking pawl to engage the second diamond-shaped portion of the shank to lock the cutting burr in the surgical drill with substantially no axial movement the locking pawl extending into the aperture provided in the spindle to engage the second diamond-shaped portion.

17. The method of claim 16, further comprising:
  replacing the cutting burr by placing the locking mechanism in the loading position;
  removing the cutting burr; and
  thereafter inserting a new cutting burr in the surgical drill when the locking mechanism is either in the running position or loading position.

18. The method of claim 16, further comprising:
  pivotally attaching the locking pawl to the spindle; and
  applying, by the locking pawl, a greater pressure to the second diamond-shaped portion as the spindle rotates.

19. The method of claim 16, wherein the detent pawl and the locking pawl have different shapes, the method further comprising:
  defining a predetermined alignment of the detent pawl and the locking pawl such that they are rotationally balanced when the cutting burr is inserted into the surgical drill and when the spindle is rotated.

20. A surgical drill, comprising:
  a cutting burr;
  a spindle rotatable about a central axis, the spindle defining a keyed slot adapted to receive a first diamond-shaped portion of a shank of the cutting burr, the spindle including opposing flattened portions defining bearing surfaces extending parallel to the central axis;
  a locking mechanism releasably mounted to the spindle;
  a locking pawl pivotally attached to the spindle and having an engagement end adapted to engage adjacent facets of a second diamond-shaped portion of the cutting burr received within the locking mechanism;
  a detent pawl having a lever pivotally connected to the spindle, the detent pawl having an engagement end portion and a biasing end portion for pivoting the engagement end portion to fit into the second diamond-shaped portion; and
  a motor for driving the spindle and the locking mechanism,
  wherein the spindle includes a first and second aperture extending through the spindle at a location between the keyed slot and the opposing flattened portions, the first and second apertures sized and configured to allow the detent pawl and the locking pawl to extend into the spindle and engage the cutting burr,
  wherein the engagement end portion of the detent pawl extends in the second diamond-shaped portion at a location opposite to where the engagement end of the locking pawl engages the cutting burr.

* * * * *